United States Patent
Althaher

(10) Patent No.: US 9,437,096 B2
(45) Date of Patent: Sep. 6, 2016

(54) SLOUCHING MONITORING AND ALERTING SYSTEM

(71) Applicant: KING FAHD UNIVERSITY OF PETROLEUM AND MINERALS, Dhahran (SA)

(72) Inventor: Ahmed Thaher Fakhri Althaher, Medinah (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 100 days.

(21) Appl. No.: 14/555,363

(22) Filed: Nov. 26, 2014

(65) Prior Publication Data
US 2016/0148481 A1 May 26, 2016

(51) Int. Cl.
G08B 23/00 (2006.01)
G08B 29/00 (2006.01)
G08B 1/08 (2006.01)
G08B 21/00 (2006.01)
A61B 5/117 (2016.01)
(Continued)

(52) U.S. Cl.
CPC ................................. *G08B 21/0446* (2013.01)

(58) Field of Classification Search
CPC  A61B 5/1116; A61B 5/0002; A61B 5/4528; A61B 5/103; A61B 17/1671; A61B 17/66; G01D 4/004; G08B 3/10; A41B 13/065; A47G 9/04; G01P 21/00; A61H 7/00
USPC ................... 340/573.7, 870.02, 539.12, 540; 600/595, 594; 601/33; 606/53–55; 128/781–782; 73/1.38
See application file for complete search history.

(56) References Cited

U.S. PATENT DOCUMENTS 3,608,541 A * 9/1971 Hall ....................... G01B 7/281
128/905
8,083,693 B1 * 12/2011 McKeon ................ A61B 5/103
600/587
(Continued)

FOREIGN PATENT DOCUMENTS

WO  WO 2014/125448 A1  8/2014

OTHER PUBLICATIONS

"What is BackPal," http://www.backpal.co.uk/, as accessed on Oct. 8, 2014, 2 pages.
(Continued)

*Primary Examiner* — George Bugg
*Assistant Examiner* — Munear Akki
(74) *Attorney, Agent, or Firm* — Richard C. Litman

(57) ABSTRACT

The slouching monitoring and alerting system includes a first patch coupled to a second patch, the first patch having a first sensor and the second patch having a second sensor, each first sensor and second sensor being configured to determine a degree of slouch, at least one connecting member connecting the first patch to the second patch, the at least one connecting member being adapted to stretch when a movement of the user varies from a pre-defined posture, an adjustment member adapted to adjust the length of the at least one connecting member, an alarm coupled to the first patch configured to generate an alert in response to a movement differing from the pre-defined posture, at least one controller/processor adapted to receive information concerning the user's posture and communicate the information with a communication device, and at least one power source.

19 Claims, 6 Drawing Sheets

(51) Int. Cl.
 *A61H 1/00* (2006.01)
 *A61F 5/04* (2006.01)
 *A61B 17/00* (2006.01)
 *G08B 21/04* (2006.01)

(56) References Cited

U.S. PATENT DOCUMENTS

| | | | |
|---|---|---|---|
| 2006/0195051 A1* | 8/2006 | Schnapp | A61B 5/1116 600/595 |
| 2008/0100459 A1* | 5/2008 | Hoffman | A61B 5/1116 340/573.7 |
| 2009/0043230 A1 | 2/2009 | Davis-Havill et al. | |
| 2013/0184611 A1* | 7/2013 | Nichols | A61B 5/04 600/587 |
| 2013/0201021 A1 | 8/2013 | Limonadi | |

OTHER PUBLICATIONS

"Spidermed 1 Audio Posture Sensor," http://physioneeds.biz/ProductDetail.aspx/Spidermed_1_Audio_Posture_Sensor/SPI01, as accessed on Oct. 8, 2014, 3 pages.

"Spidermed 2 Audio Posture Sensor," http://physioneeds.biz/ProductDetail.aspx/Spidermed_2_Audio_Posture_Sensor/SPI02, as accessed on Oct. 8, 2014, 2 pages.

"Posture Alarm Makes Your Spine Like the Queen of England's," http://gizmodo.com/292084/posture-alarm-makes-your-spine-like-the-queen-of-englands, as accessed on Oct. 8, 2014, 4 pages.

"Gadget Reminds You to Stop Slouching," http://technabob.com/blog/2007/08/20/gadget-reminds-you-to-stop-slouching/, as accessed on Oct. 8, 2014, 6 pages.

"Lumo Lift," http://www.lumobodytech.com/, as accessed on Oct. 8, 2014, 8 pages.

* cited by examiner

SLOUCHING MONITORING AND ALERTING SYSTEM

BACKGROUND OF THE INVENTION

1. Field of the Invention

The present invention relates to posture sensing and monitoring systems, and more specifically to a slouching monitoring and alerting system that provides an integrated system for collecting and analyzing data related to a person's posture.

2. Description of the Related Art

It is important for a person to maintain the correct posture throughout the day, regardless of the type of activity he/she is engaged in, such as sitting, walking, working, studying, exercising, or cooking. Certain disorders of the spine are manifested by abnormal postures. Lordosis refers to an inward, concave curvature of the spine, so that the shoulders arch posteriorly and the low back may project forward. Kyphosis refers to a convex curvature of the spine, so that the shoulders arch anteriorly and the low back may project rearward, giving the impression that the person is slouching forward. With normal posture, the shoulders and the low back are substantially straight up and down. Although not amounting to a disease, some persons adopt bad postural habits, either through laziness or inattention, adopting a lordotic slouch or a kyphotic slouch or postural position. When these habits are persistent or maintained over an extended period of time, the back becomes weak and more serious health issues may arise.

Excessive convex curvature of the spine, also known as hyperkyphosis, can result from various degenerative diseases, such as arthritis. Proper posture can lead to stronger neck, shoulder, and back muscles, while poor posture can lead to a variety of different health issues involving the neck and shoulders, as well as the upper back and lower back. The stronger a person's neck, shoulder, and back muscles the more likely these muscles can better provide support for a person. However, poor posture can translate to a weak neck, shoulder, and back muscles, as well as to chronic back pain, back injuries, and a limited range of motion and limited physical activity.

Slouching, for example, can typically lead to poor posture, and as mentioned above, may lead to health issues relating to a person's neck, shoulders, and/or back. Accordingly, to increase a likelihood of reducing such injuries a person must either refrain from slouching or correct his/her posture early in life. Currently, various devices created to correct slouching can unnecessarily limit a person's range of motion. Moreover, such devices also do not relay information to the person relating how often he/she slouches, the degree to which he/she slouches, or the duration of the slouch so that they can take appropriate corrective action to improve their posture.

Thus, a slouching monitoring and alerting system addressing the aforementioned problems is desired.

SUMMARY OF THE INVENTION

The slouching monitoring and alerting system (SMAS) is adapted to detect slouching and alert a user of the SMAS as to occurrence of a slouch. The SMAS includes a first patch or unit coupled to a second patch or unit, the first patch having a first sensor and the second patch having a second sensor, the first sensor and the second sensor being configured to determine the degree of slouch. The SMAS also includes a connecting member connecting the first patch to the second patch, the connecting member stretching when a movement of a user varies from a pre-defined posture, an adjustment member for adjusting the length of the connecting member between the first patch and the second patch, a detection and control system for receiving and analyzing information (such as the degree of slouch, the duration of the slouch, and the number of slouches in a given period of time) concerning an occurrence of the user's or the patient's slouch and for communicating information corresponding to the received and analyzed information related to an occurrence of at least one slouch to a communication device. The SMAS also includes an alarm, such as a speaker or vibrator, preferably located on the first patch that is communicatively connected to and included in the detection and control system and configured to generate an alert to notify the user of a movement differing from the pre-defined posture, and at least one power source to power the SMAS.

Further, the detection and control system can be configured so that once the connecting member is stretched, the system transmits a signal to the communication device in order to generate an alert by the communication device. It is to be noted that the alert is generated by an alert device, e.g. an alarm, located on the SMAS (such as on the first patch), and the alert generated by the communication device can be selected from various suitable alerts, such as a light alert, an audible alert, a tactile alert, or a combination thereof.

The SMAS can also include at least one counter in communication with the connecting member, as well as a first timer associated with the first sensor and a second timer associated with the second sensor. The at least one counter is configured to count the number of times a user slouches within a given period of time, while the first timer and the second timer can be configured to determine the duration of the slouch for the upper back and the lower back, respectively.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figures 1A, 1B:
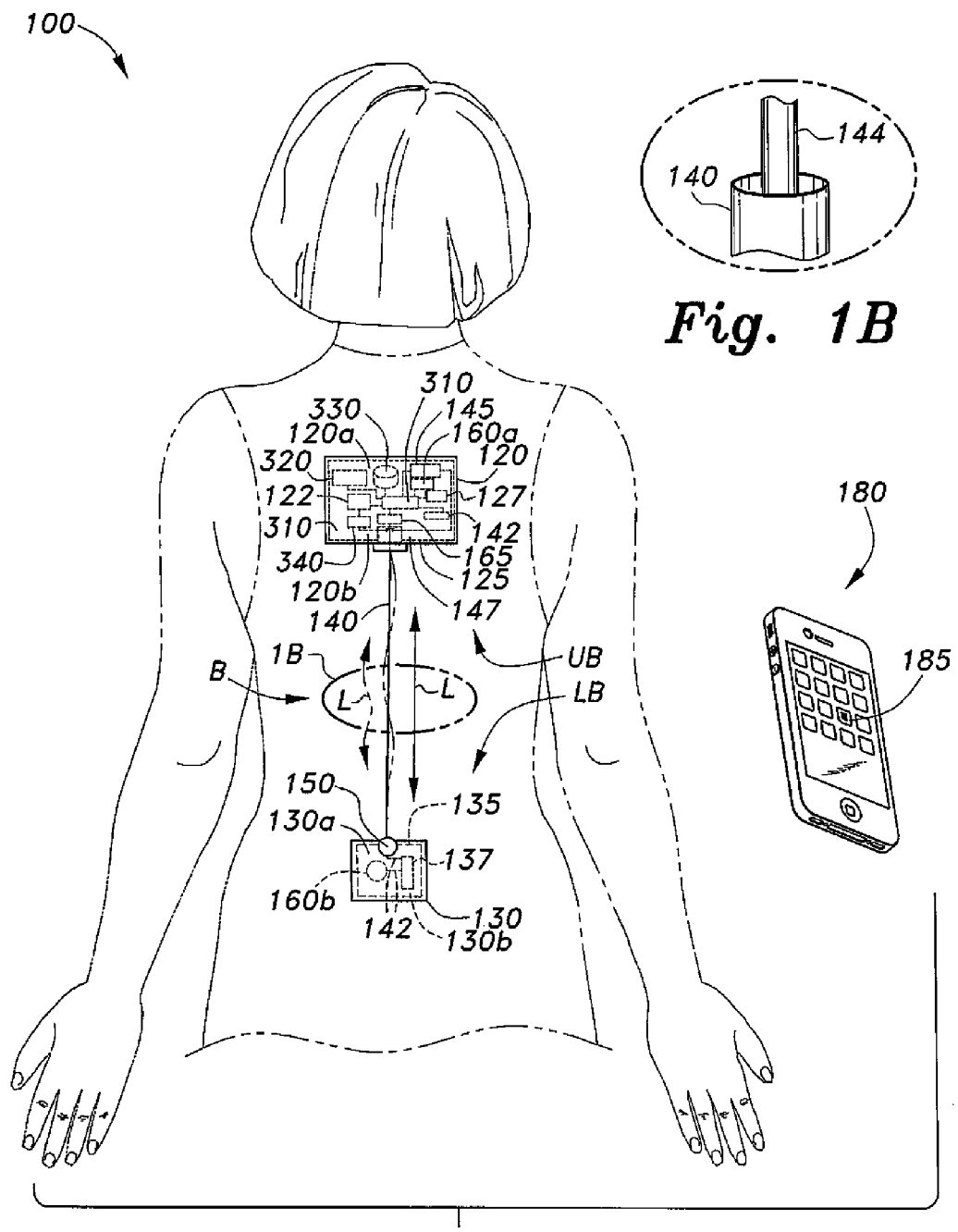
FIG. 1A is an environmental perspective view of a slouching monitoring and alerting system according to the present invention, shown attached to a user's back.
FIG. 1B is a detail view of area 1B of FIG. 1A.

Referring to FIGS. 1A-3B, the slouching monitoring and alerting system (SMAS) 100 is adapted to be positioned on the back B of a user of the SMAS 100. The SMAS 100 includes a first unit or patch 120 coupled to a second unit or patch 130, the first patch 120 being adapted to be positioned on an upper back UB of a user of the SMAS 100 and the second patch 130 being adapted to be positioned on a lower back LB of the user of the SMAS 100. Preferably, the first patch 120 and the second patch 130 are not attached to clothing, but are attached directly to the back by double-sided adhesive tape or the like. The first patch 120 has a first detection and control system 125 (shown in FIG. 3A) including a first tilt sensor 127, and the second patch 130 has a second detection and control system 135 including a second tilt sensor 137. The first sensor 127 is arranged in association with a first timer 160a of the first detection and control system 125, such as a stopwatch or other suitable timer. The second sensor 137 is arranged in association with a second timer 160b of the second detection and control system 135, such as a stopwatch or other suitable timer. While two timers 160a and 160b are preferable, the timing operations of the timers 160a and 160b can be performed by a single timer or timing circuit. The SMAS 100 also includes at least one controller/processor 310 positioned on the first patch 120. The at least one controller/processor 310 is configured to communicate with the first detection and control system 125 and the second detection and control system 135.

While the first sensor 127 and the second sensor 137 can be configured to measure a degree of slouch for the upper back UB and the lower back LB, respectively, the first timer 160a and the second timer 160b can be configured to measure the duration of the slouch for the upper back UB and the lower back LB, respectively. Further, the first detection and control system 125 and the second detection and control system 135 can be configured to communicate wirelessly with a communication device 180, such as a smartphone, a personal computer, or other computing device via a Bluetooth module 142 connected to the at least one controller/processor 310.

The SMAS 100 also includes at least one connecting member 140 and at least one counter 165. The at least one connecting member 140 can be formed from wire, rope, cable of other suitable non-conductive material so as to avoid any unnecessary contact between the at least one connecting member 140 and the back B of the user. The at least one connecting member 140 is preferably a rubber or other flexible sheath or hollow member to contain at least one electric wire 144, such as a power cable, as illustrated in FIG. 1B. This permits a single timer, housed in the first patch, and multiple counters to be housed in the first patch 120, allowing the second patch 130 to have smaller dimensions, since it houses fewer components. It is to be noted that the length of the at least one electric wire 144 will typically be equal to the length L of the connecting member 140. The at least one connecting member 140 is configured to connect the at least one counter 165 positioned on the first patch 120 and included in the first detection and control system 125 to an adjustment member 150, such as a retractable wheel, positioned on the second patch 130. The at least one counter 165 being adapted to count the number of times the user slouches in a given period of time, such as in a 24-hour period. The at least one counter 165 desirably is in communication with the at least one controller/processor 310.

The adjustment member 150, such as a retractable wheel, can be adapted to not only adjust the length L of the at least one connecting member 140, but also to maintain the length L of the at least one connecting member 140 once the at least one connecting member 140 has achieved the desired length L. The length L can correspond to a height, as well as can correspond to a weight, of the user of the SMAS 100, so as to position the first patch 120 and the second patch 130 to correspond to a pre-defined posture of the user of the SMAS 100, the pre-defined posture corresponding to a posture of the back B aligned in a substantially straight relation that does not indicate an occurrence of a slouch, for example. An alert device, such as an alarm 145, such as a speaker or vibrator, is adapted to generate an audible alert, a tactile alert, such as a vibration alert, or a combination thereof, to notify a user of the SMAS 100 of a movement differing from a pre-defined posture, such as when the at least one connecting member 140 is stretched, indicating an occurrence of a slouch, the alarm 145 being located on at least one of the first patch 120 or the second patch 130. The alarm 145, preferably located on the first patch 120, is included in the first detection and control system 125, and is in communication with the at least one controller/processor 310.

Also, the SMAS 100 includes or is adapted to include at least one power source 340 associated with the first detection and control system 125 (FIG. 3), such as a battery (which may be a rechargeable battery), that can power operation of the components of the SMAS 100, such as can respectively power the first detection and control system 125 and the second detection and control system 135, as well as all the corresponding components including the first sensor 127, the second sensor 137, the first timer 160a, the second timer 160b, the at least one counter 165, and the alarm 145, such as the speaker or vibrator.

By way of operation, the upper end of the connecting member 140 and electric cable 144 are connected to a normally open switch 147 having a biasing member, such as a spring or other suitable member, configured to keep the switch 147 in a normally open position. The switch 147 is configured to be associated with the at least one counter 165 and the alarm 145 positioned on the first patch 120, as illustrated in FIG. 3B. It is to be noted that the biasing member applies a constant force of magnitude in an opposite direction to the tension applied to the connecting member 140. As discussed herein, since the length L of the connecting member 140 has been adjusted to account for the height and weight of the user of the SMAS 100 there should not be a need to adjust the tension of the connecting member 140. It is to be noted that, typically, when the length L of the connecting member 140 is shorter, the stretching will occur faster and the switch 147 will be closed faster as compared to when the length L of the connecting member 140 is longer. As such, when a user slouches the shoulders forward in a kyphotic slouching motion and applies tension to the at least one connecting member 140, the at least one connecting member 140 stretches and pulls in an opposite direction, such as in a downward direction, to the constant force applied by the biasing member on the switch 147; thereby, closing the circuit and activating the at least one counter 165 and the alarm 145, as illustrated in FIG. 3B. The at least one counter 165 subsequently counts an occurrence of a slouch and the alarm 145 generates an alert to notify a user of the SMAS 100 of an occurrence of a slouch. It will be noted that the counter 165 and the alarm 145 are not activated until the connecting member 140 is stretched. Thus, although the tilt sensors 127, 137 will detect the tilt angles of the upper back UB and lower back LB of a person with a normally kyphotic posture, the device will not count a slouch or signal an alert until the person hunches further forward, stretching the connecting member. Thus, the device alerts the person when he or she is slouching more than normal, training the person to resume normal posture by using the normal back muscles.

As discussed herein, the at least one counter 165 counts and determines how many times a user of the SMAS 100 slouches in a given time period. Also, depending on whether the slouch is a "Little" slouch or an "Acute" slouch, to be further described, the first sensor 127 and/or the second sensor 137, is/are selectively activated to determine the degree of the slouch of the upper back UB and the lower back LB, respectively. The corresponding first timer 160a and/or second timer 160b can also be activated to determine the duration of the slouch, such as the duration of a slouch of the upper back UB and the duration of a slouch of the lower back LB, respectively.

The first sensor 127 and the second sensor 137 are configured to not only measure the degree of slouch for the upper back UB and the lower back LB, respectively, but also to communicate the corresponding information, such as the degree of the corresponding slouch for the upper back UB and for the lower back LB, to the at least one controller/processor 310, which is configured to communicate the information to the communication device 180, such as by a corresponding transmitter 320. Further, the alert generated by the alarm 145, such as from the speaker or vibrator, emitted from the SMAS 100 can include a suitable alert, such as an audible alert, a tactile alert, or a combination thereof, for example, and should not be construed in a limiting sense. It is to be noted that the first patch 120 can be adapted to include an on/off switch 122 corresponding to the first detection and control system 125 and the second detection and control system 135.

Each patch, such as the first patch 120 and the second patch 130, has two faces, a front face 120a, 130a and a back face 120b, 130b. The front face 120a, 130a of each patch 120, 130 is typically the side of the patch facing outward from the back B of the user of the SMAS 100, while the back face 120b, 130b of each patch 120, 130 is typically the side of the patch having an adhesive, such as glue or double-sided medical tape, for example, and attached to the upper back UB and the lower back LB of a user/patient using the SMAS 100, respectively.

Each patch, such as the first and second patches 120, 130, can be of any suitable size or configuration, such as having a width of about 3.5 inches and a length of about 3.5 inches, although the size or configuration can vary from the above dimensions, as can depend on the use or application, and should not be construed in a limiting sense. The corners of each patch, such as the first and second patches 120, 130, can be of various shapes or configurations, such as squared corners or corners of a generally square shape, such as illustrated in FIG. 1, and should not be construed in a limiting sense. Further, each of the first and second patches 120, 130 can be formed from any of various medically suitable materials, such as suitable plastic, cloth or rubber, or combinations thereof, as can depend on the use or application, and should not be construed in a limiting sense.

The communication device 180, such as a mobile communication device, can include an application 185, such as a mobile application, such as a slouch detection application, having programming or instructions to configure the communication device 180 to display information regarding the user or patient's posture, such as the degree of slouch for corresponding occurrence(s) of slouch(es), how many times a user of the SMAS 100 slouches in a given time period, such as in a 24-hour period, and the duration of the slouch (es), based on the input information from the first detection and control system 125 and the second detection and control system 135 corresponding to the information received from the first sensor 127 and the second sensor 137, the first timer 160a and the second timer 160b, and the at least one counter 165, for example.

Figure 1C:
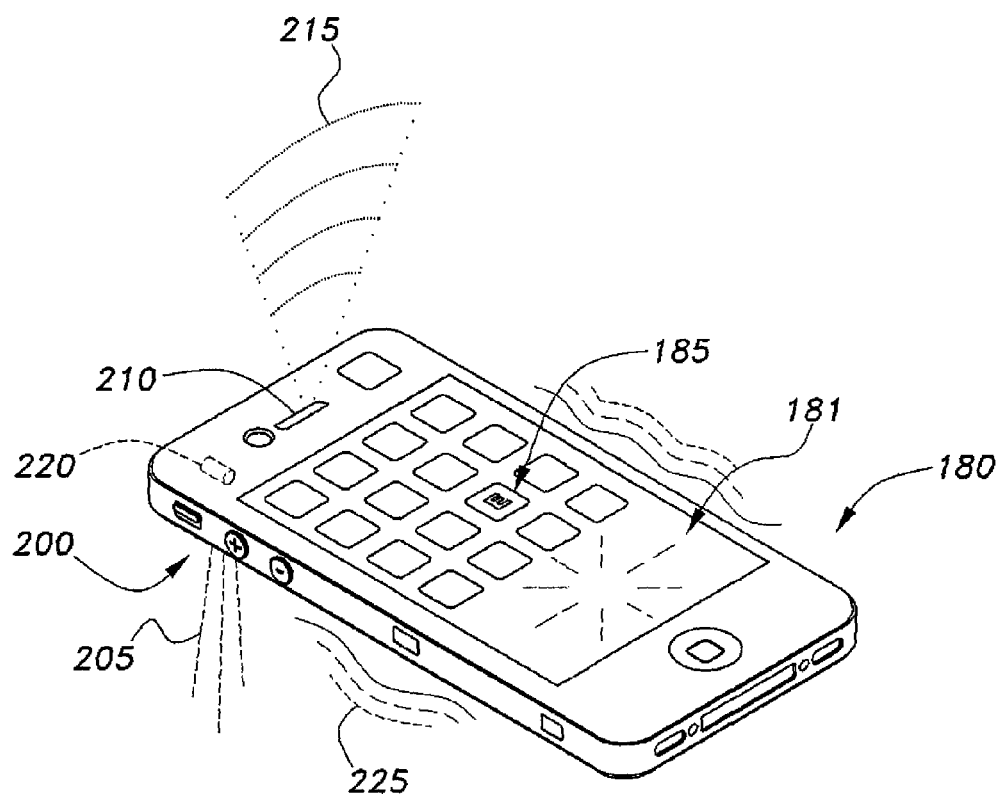
FIG. 1C is a perspective view of a communication device used in conjunction with a slouching monitoring and alert system according to the present invention.

It is to be noted that the communication device 180 can constitute and include a smartwatch, smartphone, tablet, personal computer, or a combination thereof, for example. Further, as illustrated in FIG. 1C, the communication device 180 can be configured to include a light source 200 to emit a light 205, such as can emit a steady or flashing light, a speaker 210 to emit a sound 215, and a tactile generator 220 to generate a vibration 225, and the application 185 can provide programming and instructions for the communication device 180 to generate an alert such as to emit the light 205, emit the sound 215, or generate the vibration 225, or a combination thereof.

Figure 3A:
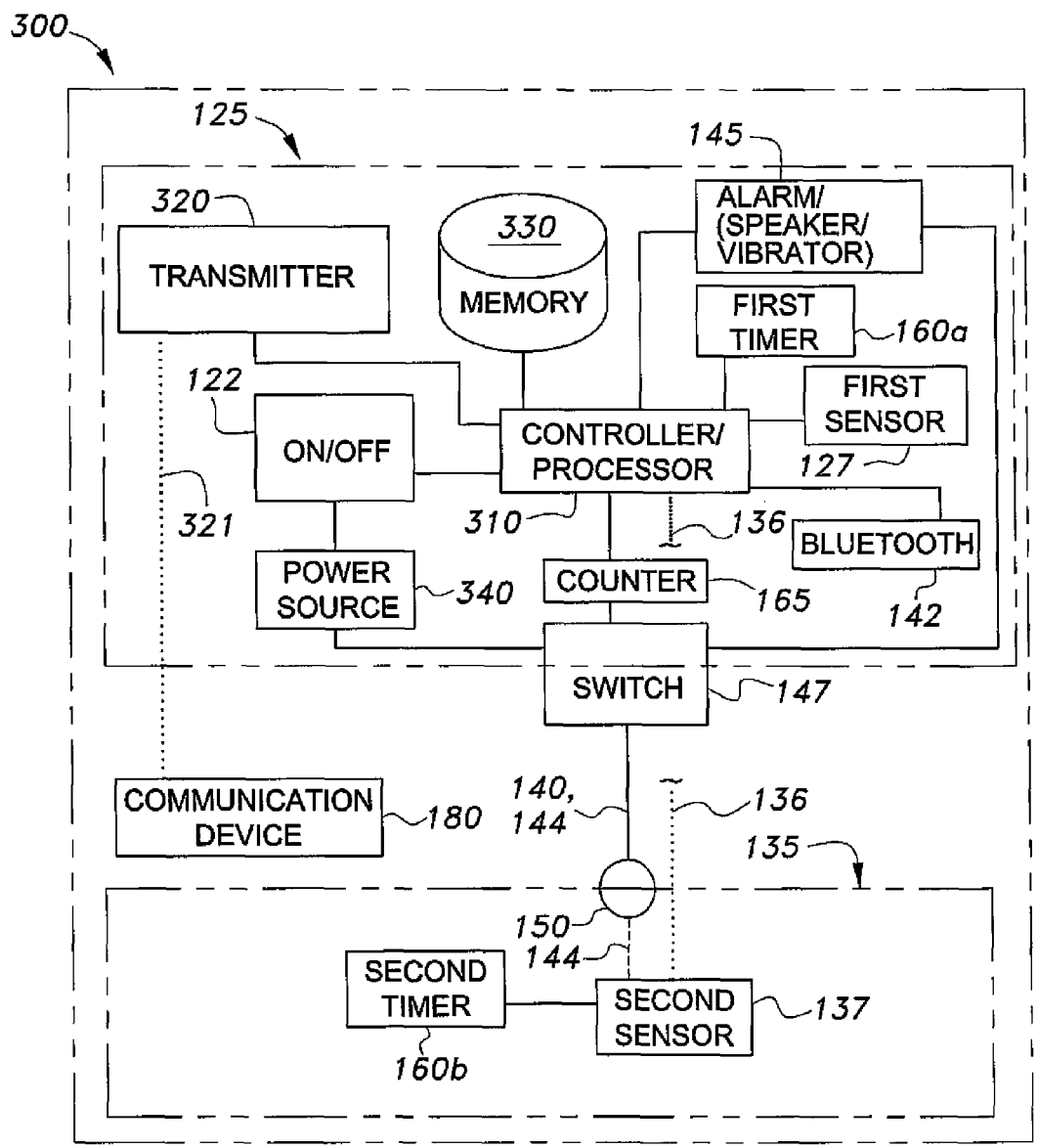
FIG. 3A is a block diagram of a slouching monitoring and alerting system according to the present invention.
Figure 3B:
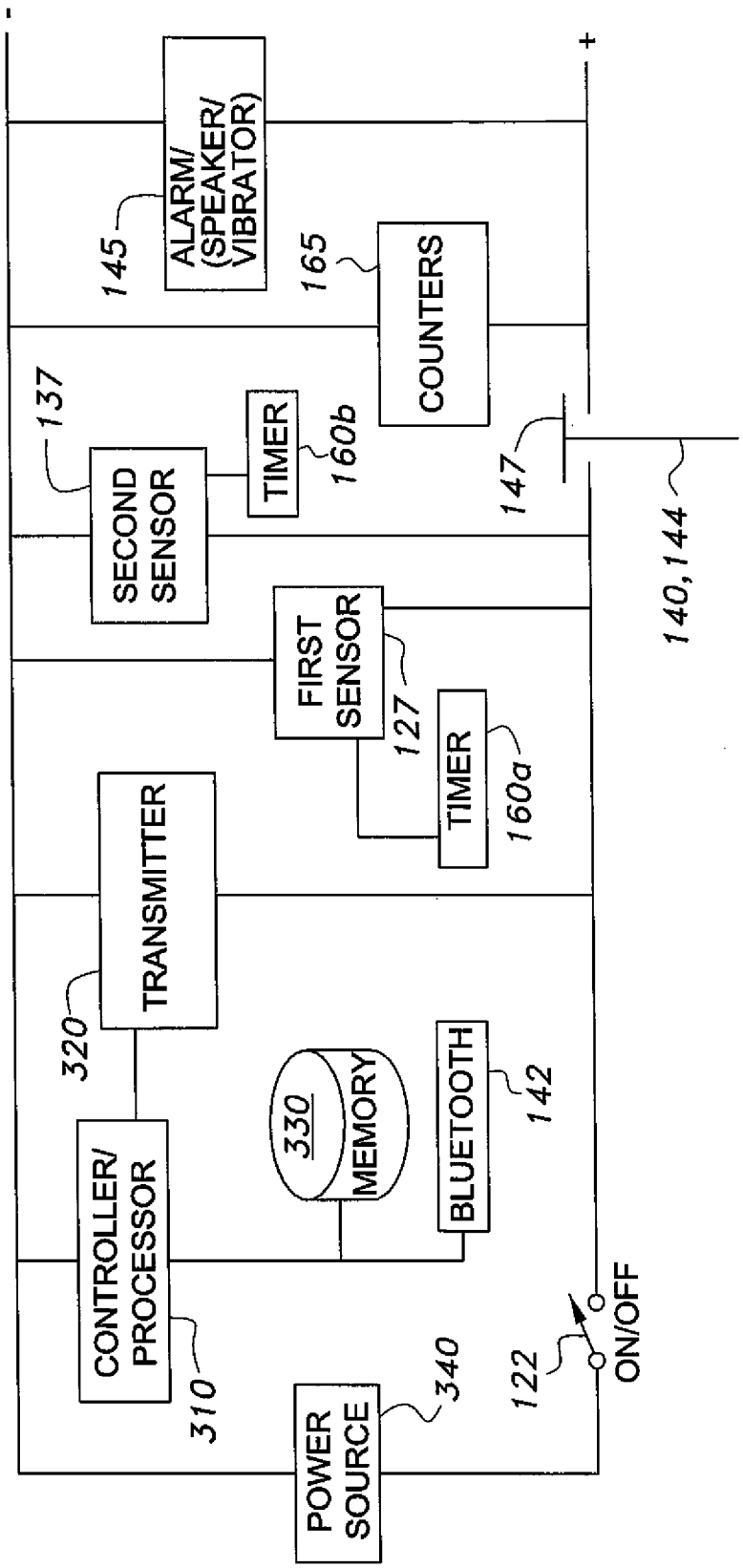
FIG. 3B is a schematic diagram of a slouching monitoring and alerting system according to the present invention.

FIG. 3A illustrates a generalized system 300 for the SMAS 100 that includes the first detection and control system 125 and the second detection and control system 135, respectively. Data reflecting or relating to the user's or patient's movement(s), such as data corresponding to an occurrence of a slouch, can be entered into the generalized system 300 as can include the first detection and control system 125 and the second detection and control system 135. The information, such as can include data, entered into the generalized system 300 can be provided to the at least one controller/processor 310 for processing and analysis, such as to the at least one controller/processor 310 that includes a processor, and the received and analyzed information can be stored in a memory 330 associated with the at least one controller/processor 310.

The at least one controller/processor 310 can be a microcontroller, an application specific integrated circuit (ASIC), or a programmable logic controller (PLC), for example, programmed with programs or instructions, as can be stored in the corresponding memory 330. Information, such as including data, is received by and entered into the generalized system 300 from any suitable type of sensor, such as the first tilt sensor 127 and the second tilt sensor 137, from the timer, such as the first timer 160a associated with the first sensor 127 and the second timer 160b associated with the second sensor 137, and from the at least one counter 165 in communication with the at least one connecting member 140, as can be associated in communicating relation with the at least one controller/processor 310.

The generalized system 300 also includes the transmitter 320 (and/or a Bluetooth module 142 for communication with smartphones that are Bluetooth-enabled) associated with the first detection and control system 125, the at least one controller/processor 310, and with the second detection and control system 135, such as for wireless transmission or for wireless communication of information from the at least one controller/processor 310, such as can include data or control signals, to the communication device 180, as can also be a wired communication or transmission, relating to the posture or occurrence of slouch(es) of a user, such as can be a patient, using the SMAS 100. The communication or the transmission of information, such as can include data or control signals, from the transmitter 320 to the communication device 180, is respectively indicated by the dotted lines 321. The communication device 180 in addition to being a mobile communication device, can also be any other suitable computing device, such as a standalone computer, computer terminal, portable computing device, networked computer or computer terminal, or networked portable device that can include a microcontroller, an ASIC, or a PLC, for example, as well as can include an associated display.

Further, it is to be noted that the first detection and control system 125 can be configured to include the memory 330 and the second detection and control system 135 can be configured to communicate with the memory 330, such as through the electric wire 144. The memory 330 can be adapted to store data and information, as well as program(s) or instructions for implementing operation of the SMAS 100. The memory 330 can be any suitable type of computer readable and programmable memory, such as non-transitory computer readable media, random access memory (RAM) or read only memory (ROM), for example. The generalized system 300 can also be powered by the at least one power source 340, such as a battery.

Calculations, determinations, or data transmission, the sending or receiving of control signals or commands, or providing information in relation to the user's posture, such as an occurrence of a slouch, are performed or executed by the at least one controller/processor 310 positioned on the first patch 120. Also, the functions of the at least one controller/processor 310 can also be performed by an integrated single controller/processor in the generalized system 300.

The at least one controller/processor 310 can be any suitable type of computer processor, such as a microprocessor, a PLC or an ASIC, such as can be programmed with instructions to execute calculations, determinations, data transmission or data reception, sending or receiving of control signals or commands processed or controlled by the at least one controller/processor 310. Information, such as related to an occurrence of at least one slouch, can be displayed to the user of the SMAS 100 on a display 181 of the communication device 180 having the application 185, or can be displayed on a suitable display associated with the communication device 180.

The at least one controller/processor 310 can be associated with, or incorporated into, any suitable type of computing device, such as a PLC or an ASIC. The components of the first detection and control system 125, such as the first sensor 127, the first timer 160a, and the at least one counter 165, and the components of the second detection and control system 135, such as the second sensor 137, the second timer 160b, as well as the at least one controller/processor 310, the memory 330, the transmitter 320, and any associated computer readable media are in communication with one another by any suitable type of data bus, as is well known in the art. Also, the first detection and control system 125 and the components thereof included on the first patch 120 and the second detection and control system 135 and the components thereof included on the second patch 130 can be respectively formed as part of a corresponding integrated circuit (IC) chip, for example. It is to be noted that while the switch 147 is required to be closed by the tension on the connecting member 140 and corresponding electric wire 144 so as to activate the at least one counter 165 and alarm 145, once the on/off switch 122 is turned to the "on" position all the components including the at least one controller/processor 310, the memory 330, the Bluetooth module 142, the transmitter 320, the first sensor 127 and corresponding first timer 160a, as well as the second sensor 137 and corresponding second timer 160b are active and operational, as illustrated in FIG. 3B.

Figure 2A:
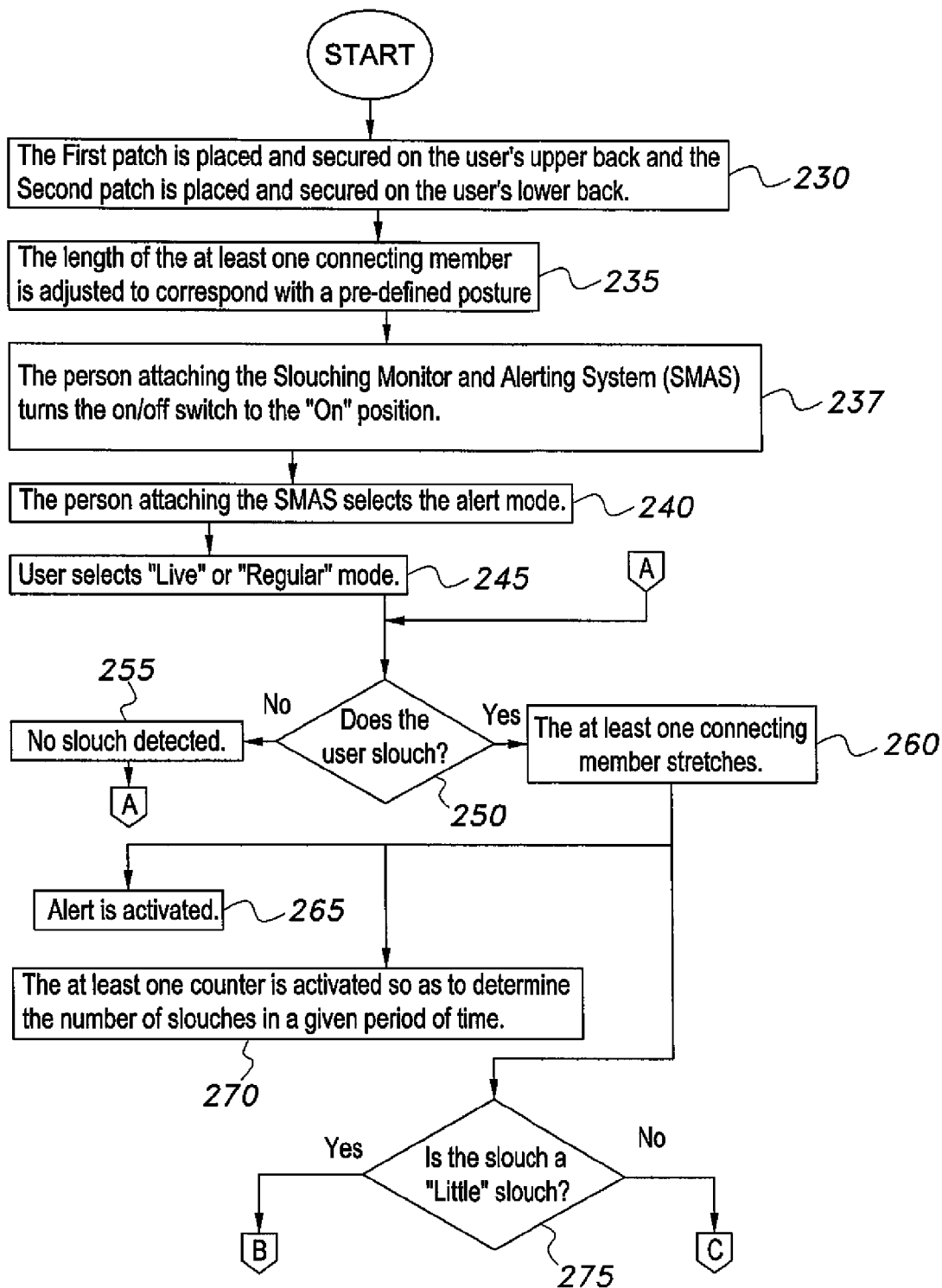
FIGS. 2A and 2B show a flowchart illustrating steps in a method for monitoring occurrence of a slouch in a slouching monitoring and alerting system according to the present invention.
Figure 2B:
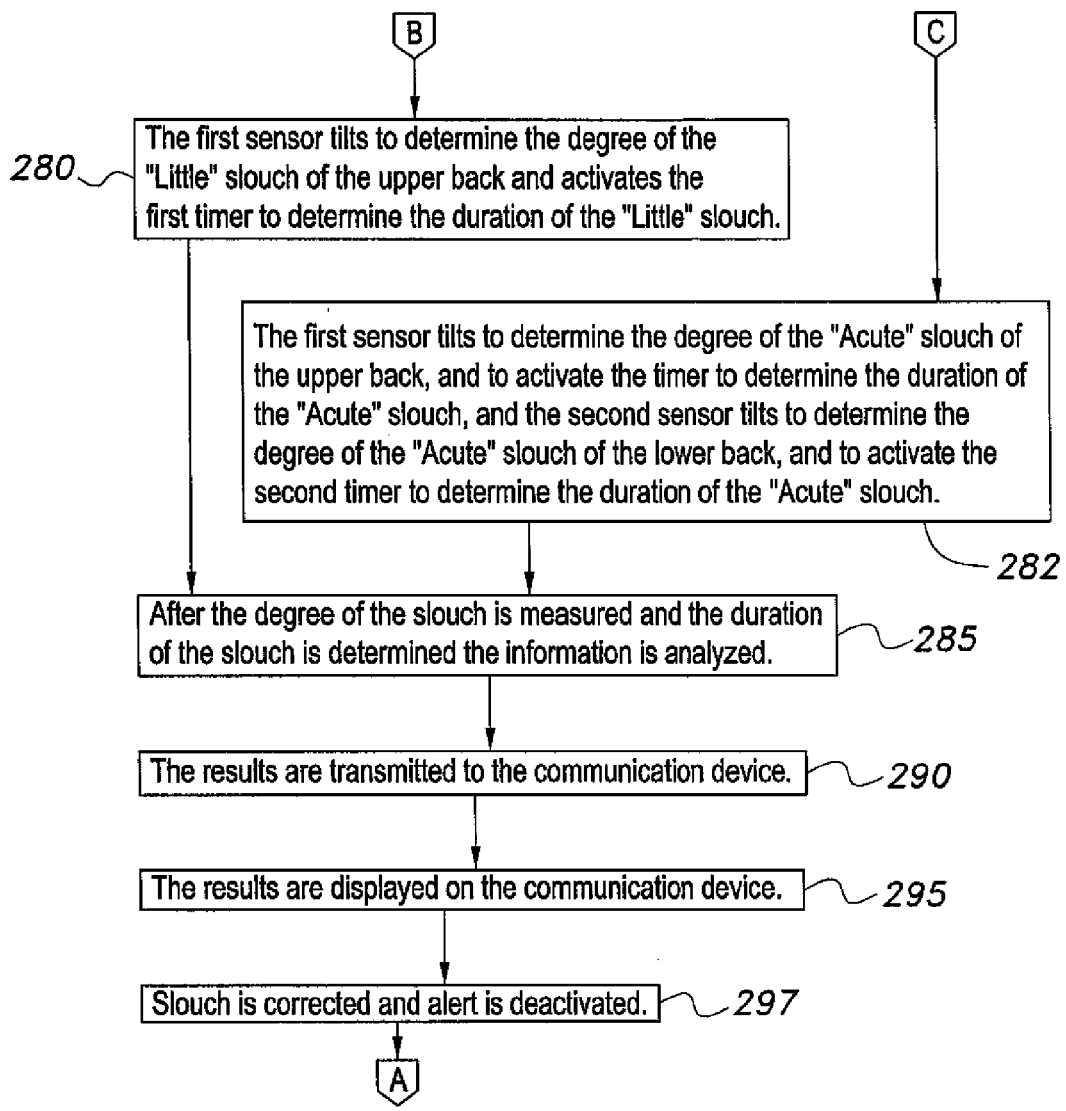

Referring to FIGS. 2A and 2B, flowcharts of processes or steps of embodiments of methods for monitoring an occurrence of a slouch using the SMAS 100 are illustrated. By way of operation, the first patch 120 is placed and secured on the user's upper back UB, such as positioned in the center of the upper back UB below the neck and between the shoulder blades, and the second patch 130 is placed and secured on the user's lower back LB, such as positioned in the center of the lower back LB on the user's lower lumbar region (Step 230). The first patch 120 and the second patch 130 can be secured to the user's back B using suitable glue or other suitable adhesive, such as double-sided medical tape, so as to minimize the occurrence of the first patch 120 and the second patch 130 from accidentally detaching from the user's back 13.

The length L of the at least one connecting member 140 is adjusted so as to position the first patch 120 and the second patch 130 to correspond to a pre-defined posture, as can correspond with the user's height, as well as can be related to a user's weight, in determining an appropriate length L for the at least one connecting member 140 (Step 235). The length L of the at least one connecting member 140 can be controlled by the adjustment member 150, such as can be a retractable wheel or spool. For example, the at least one connecting member 140, such as flexible wire, cable, rubber, or rope, can be coiled or wound around the adjustment member 150 until the desired length L is achieved, the adjustment member 150 securing the at least one connecting member thereon at the desired length L. Further, while the at least one connecting member 140 should be substantially taut, the at least one connecting member 140 should have sufficient "give" so as to be able to "stretch" to a degree from the desired length L so as not to unnecessarily limit the user's range of motion.

Once the SMAS 100 is secured to the user's back B, positioned to correspond to a pre-defined posture, or before the SMAS 100 is secured to the user's back B, the person attaching the SMAS 100, as can be a user of the SMAS 100, can activate the SMAS 100 by turning the on/off switch 122 to the "on" position (Step 237) and, subsequently, can select an alert mode, such as by operation of a selection switch associated with the alarm 145, (Step 240) so that the alarm 145 of the SMAS 100 generates an alert by the alarm 145, such as by emitting either an audible alert, a tactile alert, or a combination thereof to notify the user of the SMAS 100 as to the occurrence of a slouch. The person attaching the SMAS 100 can also select from either a "Live" mode or a "Regular" mode (Step 245), such as by entering or selecting the "Live" mode or the "Regular" mode on the communication device 180. The "Live" mode enables the user to view their posture as an image displayed in real time on the display 181 of the communication device 180 from the information received from the first detection and control system 125 and the second detection and control system 135, and the "Regular" mode simply alerts the user to the occurrence of a slouch and allows the user to retrieve any stored information relating to past slouches at a later time.

It is to be noted that the alarm 145 provides an alert when the user's body is in a relatively bad or undesirable posture, such as when an occurrence of a slouch is detected. It must be noted that a slouch occurs when the at least one connecting member 140 is stretched due to an increase in the distance between the first patch 120 and the second patch 130. This makes the device particularly useful for detecting a slouch into a kyphotic posture. Moreover, when the SMAS 100 detects a slouch, such as can be a "Little" slouch or an "Acute" slouch, the sensors, such as the first sensor 127 and the second sensor 137, detect a corresponding degree of slouch. Further, the corresponding timers, such as the first timer 160a and second timer 160b, will be activated if the sensors, such as the first senor 127 and second sensor 137, are in a tilted position or indicate a tilt, such as relative to an initial "no-tilt" position.

If, for example, a user has a "healthy" posture in which the upper back UB and the lower back LB are substantially straight, no alerts by the alarm 145 will be generated or emitted and, since the sensors, such as the first sensor 127 and second sensor 137, are not in a tilted position or not indicating a tilt, the corresponding timers, such as the first timer 160*a* and second timer 160*b*, will not be activated. Another example of a "healthy" posture is when a person bends the back B relatively straight from the waist toward the ground. In this posture, the spine typically, and therefore the back B, remains substantially straight as in a "healthy" posture, as the back B bends substantially only from the body's waist, as can enhance strengthening of the person's back B. It should be noted that the at least one connecting member 140 typically will not stretch during the "healthy" postures.

Once the SMAS 100 has been turned on and configured accordingly, the user of the SMAS 100 can go about normal day activities, such as running, walking, lifting, standing, sitting, or a combination thereof. When the SMAS 100 is on, the SMAS 100 monitors and determines whether the user slouches (Step 250). If the user does not slouch, no slouch is detected (Step 255) and the user can continue about his/her day without the SMAS 100 generating or emitting an alert, such as by the alarm 145. When an occurrence of a slouch is not detected by the SMAS 100 (Step 255), the process returns to Step 250. If a slouch occurs by the person using the SMAS 100 (Step 250), the process then continues as described below.

If the user slouches (Step 250), the at least one connecting member 140 stretches (Step 260) and puts tension on the at least one connection member 140 and corresponding electric wire 144. Once the at least one connecting member 140 stretches (Step 260), the switch 147 is closed and an alert by the alarm 145 is activated (Step 265), such as an audible alert that can be heard through the speaker of the alarm 145, or a tactile alert through the vibrator of the alarm 145, or a combination thereof, to notify the user of the occurrence of a slouch. It is to be noted that once the at least one connecting member 140 is stretched (Step 260), the first detection and control system 125 and the second detection and control system 135 can be configured to transmit information, such as can include a control signal, to the communication device 180 so as to generate the light 205 from the light source 200, the sound 215 from the speaker 210, the vibration 225 from the tactile generator 220, such as a piezoelectric vibration generator, or a combination thereof, as illustrated in FIG. 1B.

Further, the SMAS 100 can be configured for the alarm 145 to generate an alert, such as by emitting an audible alert from the alarm 145, for a predetermined period of time, such as for approximately 10 seconds, and if, after approximately 10 seconds, the slouch is not corrected a second audible alert, such as a double alert will be emitted by the alarm 145 until the slouch is corrected, such as when a slouch is no longer detected. Additionally, it is to be noted that when the at least one connecting member 140 stretches and closes the switch 147, the at least one counter 165 is activated to count the occurrence of the slouch so as to determine the number of slouches in a given period of time (Step 270), and the at least one counter 165 provides the count information corresponding to the occurrence of the current slouch, as well as can provide a total of the occurrence of slouches within a predetermined time period, to the at least one controller/processor 310.

Then, it is determined if the slouch corresponds to a "Little" slouch (Step 275). A "Little" slouch can be defined as a slouching of the upper back UB and maintaining a substantially straight lower back LB. The "Little" slouch typically occurs in offices and restaurants when people sit on low back chairs, for example. If the slouch is determined not to be a "Little" slouch, then the slouch is determined as corresponding to an "Acute" slouch. An "Acute" slouch, on the other hand, can be defined as slouching of both the upper back UB and the lower back LB. The "Acute" slouch typically occurs while sitting on the floor. If the slouch is determined to be a "Little" slouch, the first sensor 127 typically tilts or indicates a tilt to determine the degree of slouching corresponding to the "Little" slouch of the upper back UB and provides the degree of slouching of the upper back UB to the at least one controller/processor 310 to activate the corresponding first timer 160*a* to determine the duration of the "Little" slouch (Step 280). The degree of slouch "D" for a "Little" slouch and the degree of slouch "D" for an "Acute" slouch can be numerical value corresponding to the type of slouch, such as a "Little" slouch or an "Acute" slouch, as well as can be a numerical value corresponding to a degree of slouch as measured by the first sensor 127 and the second sensor 137, as can depend on the severity of the slouch, or a combination thereof, for example.

For the occurrence of a "Little" slouch, one or more of the first sensor 127 and corresponding first timer 160*a*, the second sensor 137 and corresponding second timer 160*b*, and the at least one counter 165, will have detected corresponding information, such as a corresponding degree of slouch, a duration of the slouch, and a slouching number, such as the number of slouches within a given period of time. The information is then provided to at least one of the controller/processor 310 and analyzed (Step 285), such as by the at least one controller/processor 310. Communication of information related to a slouch between the at least one controller/processor 310 and the first detection and control system 125 and the second detection and control system 135 can be by a suitable bus, or can be by wireless transmission, such as by a transmitter/receiver incorporated as a transceiver in the transmitter 320, such as indicated by the dotted line 136 or through the connection member 140 and its corresponding at least one electric wire 144, such as illustrated in FIG. 3A.

Information related to the occurrence of at least one slouch, such as data and the results of the analysis of the detected of one or more "Little" slouches, is transmitted to the communication device 180, such as by the transmitter 320, such as by desirably wireless or by wired transmission (Step 290). Depending on whether the user has selected the "Live" mode or the "Regular" mode, the results of the analysis of the detected one or more slouches will be displayed on the display 181 of the communication device 180 (Step 295). Once the currently detected "Little" slouch is corrected by the user of the SMAS 100, such as by straightening the user's back B and, in turn, returning the at least one connecting member 140 to its original un-stretched length L for the user of the SMAS 100, the alert by the alarm 145 is deactivated (Step 297). Once the slouch is corrected and the alert by the alarm 145 has been deactivated, the process returns to Step 250 and continues as described.

If, however, it is determined the slouch is not a "Little" slouch at Step 275, but instead a slouch including both the upper back UB and the lower back LB, including, but not limited to, a slouch that changes from a "Little" slouch to an "Acute" slouch, the first sensor 127 determines the degree of slouch of the upper back UB and the second sensor 137 determines the degree of slouch for the lower back LB corresponding to an "Acute" slouch. The degree of slouch can be determined by measuring a range or an amount of tilt by the corresponding first and second sensors 127, 137 caused by a corresponding slouch to determine a corresponding degree of slouch, for example (Step 282).

Further, the corresponding first timer 160a and the second timer 160b are respectively selectively activated to determine the duration of time for the "Acute" slouch. If the slouch has changed from a 'Little" slouch to an "Acute" slouch, the first timer 160a also determines the total duration of the time for the slouch that includes the time for the "Little" slouch and the time for the "Acute" slouch. After the first sensor 127 and the corresponding first timer 160a and the second sensor 137 and the corresponding second timer 160b determine the degree of and duration of time for the "Acute" slouch for the upper back UB and the lower back LB, respectively, at Step 282 the process goes to Step 285 and similarly continues as previously described for steps 285, 290, 295 and 297 but in relation to the detected "Acute" slouch.

As discussed above, each time a slouch is detected, it will be counted by the at least one counter 165 coupled to the at least one connecting member 140, and, depending on whether the slouch is a "Little" slouch or an "Acute" slouch, the first sensor 127 and the corresponding first timer 160a and the second sensor 137 and the corresponding second timer 160b will be selectively activated to determine the degree of slouch, such as the degree of the slouch of the upper back UB and of the lower back LB, respectively, and the duration of time of the slouch of the upper back UB and of the lower back LB, respectively. Accordingly, each slouch will have a corresponding degree of slouch and duration of the slouch.

It must be noted that while the first sensor 127 and the corresponding first timer 160a will be activated in both "Little" and "Acute" slouches, the second sensor 137 and the corresponding second timer 160b will only be activated when the user of the SMAS 100 undergoes an "Acute" slouch in which the user slouches his/her lower back LB. To determine the duration of the "Little" slouch, since the "Little" slouches are different from "Acute" slouches, as described, the duration of time for the "Acute" slouch will be subtracted from the total duration of the entire slouch.

For example, a slouch, which lasts for a total of three minutes, one minute of which is an "Acute" slouch, will translate into a "Little" slouch of two minutes and an "Acute" slouch of one minute. This relationship can be described by the following mathematical relation or formula, such as can be determined by the at least one controller/processor 310:

$$\text{Duration of "Little" slouch} = \text{Total Duration of Slouch} - \text{Duration of "Acute" slouch}. \quad (1)$$

The data relating to the type of slouch, the duration of the corresponding slouch and the analysis thereof can be stored in the memory 330 and then corresponding information can be transmitted, such as wirelessly transmitted, to the communications device 180, as described. The information, such as can include data, determinations and analyses, corresponding to one or more slouches transmitted to the communication device 180, can enable the user of the SMAS 100 to see, such as displayed on the display 181 of the communication device 180, the amount of times the user slouches in a given period of time (such as in a 24-hour period), the percentage of improvement in the number of the slouches for a first time period compared with a number of slouches for a second time period (such as the number of slouches in the current week compared to the number of slouches for the past week), the total duration of "Little" slouches compared with "Acute" slouches for a predetermined time period, such as for each day, the percentage of improvement in degree of slouching (such as the duration of "Acute" slouches compared to the duration of "Little" slouches), as well as the "score of the day" corresponding to a sum of "slouch scores", which represents the sum of each of the periods of slouching for a day, or other suitable time period, each "slouch score" corresponding to a period of time of slouching multiplied by a corresponding degree of slouch for the respective period of time.

The above described determinations as can be displayed on the display 181 of the communication device 180 can be determined by executing corresponding programming or instructions by a controller/processor of the communication device 180, such as by executing corresponding programming or instructions of the application 185, for example, and/or can be determined at least in part by the at least one controller/processor 310 by executing corresponding programming or instructions.

Also, the relationship for the above described score of the day can be described by the following mathematical relation or formula:

$$\text{Score of the Day} = (T_1 * D_1) + (T_2 * D_2) + (T_3 * D_3) + (T_4 * D_4) + \ldots (T_n * D_n). \quad (2)$$

In the above formula or relation (2), $T_1, T_2, \ldots T_n$ is the duration of a corresponding slouch, $D_1, D_2, \ldots D_n$ is the corresponding degree of slouch and $(T_1 * D_1) + (T_2 * D_2) + (T_3 * D_3) + (T_4 * D_4) + \ldots (T_n * D_n)$ are each "slouch scores". It must be noted that for "Acute" slouches, the degree of the "Acute" slouch should be multiplied by its corresponding time duration after the formula or relation (1) is applied to determine the duration of the corresponding "Acute" slouch. Further, if the "Live" mode is selected, the user of the SMAS 100 can see the slouching degree for one or more corresponding slouches and other data, as described, on the display 181 of the communication device 180 in real time.

It is to be understood that the present invention is not limited to the embodiments described above, but encompasses any and all embodiments within the scope of the following claims.

I claim:

1. A slouching monitoring and alerting system, comprising:
   a first patch and a second patch, the first patch adapted to be coupled to the second patch, the first patch having a first tilt sensor configured for sensing tilt of a user's upper back and the second patch having a second tilt sensor configured for sensing tilt of the user's lower back, the first sensor and the second sensor being configured to determine a degree of slouch for an occurrence of a slouch and each of the first timer and the second timer configured to measure a corresponding duration of a corresponding slouch;
   at least one connecting member connecting the first patch to the second patch, the at least one connecting member being adapted to stretch when a movement of a user of the slouching monitoring and alerting system varies from a pre-defined posture to indicate an occurrence of a slouch;
   an adjustment member adapted to selectively adjust a length of the at least one connecting member between the first patch and the second patch so as to position the first patch and the second patch to correspond to the pre-defined posture of the user;
   an alarm coupled to at least one of the first patch or the second patch, the alarm configured to generate an alert adapted to notify the user of a movement differing from the pre-defined posture to indicate the occurrence of a corresponding slouch, the alarm being disposed in a circuit having a normally open switch connected to the connecting member so that stretching the connecting member closes the circuit and activates the alarm;

at least one controller/processor adapted to receive information from the first sensor and the second sensor and adapted to communicate information related to an occurrence of at least one slouch with a communication device;

means for selectively determining by the at least one controller/processor of the slouching monitoring and alerting system if the degree of slouch corresponds to a "Little" slouch associated with movement of the upper back detected by the first sensor or if the degree of slouch corresponds to an "Acute" slouch associated with movement of the upper back detected by the first sensor and movement of the lower back detected by the second sensor, based on information received by the at least one controller/processor from the first sensor and the second sensor; and means for transmitting information related to at least one occurrence of a slouch to a communication device.

2. The slouching monitoring and alerting system according to claim 1, further comprising at least one counter arranged in communication with the at least one connecting member, the at least one counter configured to count a number of times of an occurrence of a slouch in a given period of time, the at least one counter being disposed in the circuit with said normally open switch so that a slouch is counted only when said connecting member is stretched.

3. The slouching monitoring and alerting system according to claim 1, wherein the adjustment member comprises a retractable wheel.

4. The slouching monitoring and alerting system according to claim 1, further comprising the communication device, the communication device being configured to indicate an alert, based on the communicated information related to the occurrence of at least one slouch, the alert generated by the communication device being selected from the group consisting of a visual alert, an audible alert, tactile alert, or a combination thereof, the communication device, based on the information communicated by the at least one controller/processor, being adapted to display at least one of the amount of times the user slouches in a given period of time, a percentage of improvement in a number of slouches for a first time period compared with a number of slouches for a second time period, a total duration of "Little" slouches of an upper back of the user compared with "Acute" slouches of the upper back and a lower back of the user for a predetermined time period, a percentage of improvement in degree of slouching of a duration of the "Acute" slouches compared to a duration of the "Little" slouches, and a "score of the day" corresponding to a sum of "slouch scores", each "slouch score" corresponding to a period of time of slouching multiplied by a corresponding degree of slouch for the respective period of time.

5. The slouching monitoring and alerting system according to claim 1, further comprising a Bluetooth module connected to the at least one controller/processor for communicating wirelessly with the communication device.

6. The slouching monitoring and alerting system according to claim 5, wherein the communication device is selected from the group consisting of a smartwatch, a smartphone, a tablet, and a personal computer.

7. A slouching monitoring and alerting system, comprising:

a first patch and a second patch, the first patch adapted to be coupled to the second patch, the first patch having a first tilt sensor configured for sensing tilt of a user's upper back and the second patch having a second tilt sensor configured for sensing tilt of the user's lower back, the first sensor and the second sensor being configured to determine a degree of slouch for an occurrence of a slouch and each of the first timer and the second timer configured to measure a corresponding duration of a corresponding slouch;

at least one connecting member connecting the first patch to the second patch, the at least one connecting member being adapted to stretch when a movement of a user of the slouching monitoring and alerting system varies from a pre-defined posture to indicate an occurrence of a slouch;

an adjustment member adapted to adjust the length of the at least one connecting member between the first patch and the second patch so as to position the first patch and the second patch to correspond to the pre-defined posture of the user;

a first timer associated with the first sensor and a second timer associated with the second sensor, the first timer and the second timer configured to measure a corresponding at least one duration of time of a corresponding at least one slouch;

an alarm coupled to at least one of the first patch or the second patch, the alarm being configured to generate an alert adapted to notify the user of a movement differing from the pre-defined posture, the alarm being disposed in a circuit having a normally open switch connected to the connecting member so that stretching the connecting member closes the circuit and activates the alarm;

at least one controller/processor adapted to receive information from the first sensor and the first timer and from the second sensor and the second timer and adapted to communicate information related to an occurrence of at least one slouch with a communication device;

means for selectively determining by the at least one controller/processor of the slouching monitoring and alerting system if the degree of slouch corresponds to a "Little" slouch associated with movement of the upper back detected by the first sensor or if the degree of slouch corresponds to an "Acute" slouch associated with movement of the upper back detected by the first sensor and movement of the lower back detected by the second sensor, based on information received by the at least one controller/processor from the first sensor and the second sensor; and means for transmitting information related to at least one occurrence of a slouch to a communication device.

8. The slouching monitoring and alerting system according to claim 7, further comprising at least one counter arranged in communication with the at least one connecting member, the at least one counter configured to count a number of times the user slouches in a given period of time, the at least one counter being disposed in the circuit with said normally open switch so that a slouch is counted only when said connecting member is stretched.

9. The slouching monitoring and alerting system according to claim 7, wherein the adjustment member comprises a retractable wheel.

10. The slouching monitoring and alerting system according to claim 7, wherein the alert generated by the alarm is selected from the group consisting of an audible alert and a tactile alert, or a combination thereof.

11. The slouching monitoring and alerting system according to claim 7, further comprising a Bluetooth module connected to the at least one controller/processor for communicating wirelessly with the communication device.

12. The slouching monitoring and alerting system according to claim 11, further comprising the communication device, the communication device being selected from the group consisting of a smartwatch, a smartphone, a tablet, a personal computer, or a combination thereof.

13. A method for monitoring slouches, the method comprising the steps of:
(a) coupling a first patch to a second patch of a slouching monitoring and alerting system by at least one connecting member, the at least one connecting member being adapted to stretch when a movement of a user of the slouching monitoring and alerting system varies from a pre-defined posture to indicate an occurrence of a slouch, the first patch having a first sensor and a first timer and the second patch having a second sensor and a second timer, each of the first sensor and the second sensor being configured to determine a degree of slouch for a corresponding at least one slouch, and each of the first timer and the second timer configured to measure a corresponding duration of a corresponding at least one slouch;
(b) adjusting a length of the at least one connecting member between the first patch and the second patch by an adjustment member so as to position the first patch and the second patch to correspond to the pre-defined posture of the user;
(c) positioning the first patch on an upper back of the user and the second patch on a lower back of the user corresponding to the pre-defined posture;
(d) detecting a stretching of the at least one connecting member corresponding to movement of the user that is different from the pre-defined posture;
(e) when the stretching of the at least one connecting member is detected in step (d), determining, by the first sensor, a degree of slouch of the upper back and activating the first timer to determine a duration of a corresponding slouch of the upper back and, when the stretching of the at least one connecting member is detected in step (d) and an occurrence of a slouch of the lower back is indicated, determining, by the second sensor, a degree of slouch of the lower back and activating the second timer to determine a duration of a corresponding slouch of the lower back;
(f) selectively generating an alert by an alarm associated with the slouching monitoring and alerting system in response to the detected movement that differs from the pre-defined posture;
(g) when the stretching of the at least one connecting member is detected in step (d), receiving information by at least one controller/processor of the slouching monitoring and alerting system corresponding to the degree of slouch of the upper back detected by the first sensor and a measured duration of time of the corresponding slouch of the upper back from the first timer and, when the stretching of the at least one connecting member is detected in step (d) and an occurrence of a slouch of the lower back is indicated, receiving information by the at least one controller/processor corresponding to the degree of slouch of the lower back detected by the second sensor and a measured duration of time of the corresponding slouch of the lower back from the second timer;
(h) selectively determining by the at least one controller/processor of the slouching monitoring and alerting system if the degree of slouch corresponds to a "Little" slouch associated with movement of the upper back detected by the first sensor or if the degree of slouch corresponds to an "Acute" slouch associated with movement of the upper back detected by the first sensor and movement of the lower back detected by the second sensor, based on information received by the at least one controller/processor from the first sensor and the second sensor; and
(i) transmitting information related to at least one occurrence of a slouch to a communication device.

14. The method for monitoring slouches according to claim 13, further comprising:
selectively counting by a counter of the slouching monitoring and alerting system a number of slouches within a given period of time.

15. The method for monitoring slouches according to claim 13, wherein the adjustment member comprises a retractable wheel.

16. The method for monitoring slouches according to claim 13, wherein the alert is selected from the group consisting of an audible alert and a tactile alert, or a combination thereof.

17. The method for monitoring slouches according to claim 13, wherein the at least one controller/processor is adapted to communicate wirelessly with the communication device.

18. The method for monitoring slouches according to claim 13, wherein the communication device is selected from a group consisting of a smartwatch, a smartphone, a tablet, and a personal computer.

19. The method for monitoring slouches according to claim 18, further comprising the step of:
generating an alert by the communication device based on the transmitted information related to at least one occurrence of at least one of the "Little" slouch and the "Acute" slouch,
wherein the alert generated by the communication device is selected from the group consisting of a visual alert, an audible alert, tactile alert, or a combination thereof, and
wherein the alert generated by the alarm is selected from the group consisting of an audible alert, a tactile alert, or a combination thereof.

* * * * *